United States Patent [19]

Franz

[11] 4,147,719

[45] Apr. 3, 1979

[54] PROCESS FOR PRODUCING N-PHOSPHONOMETHYLGLYCINE SALTS

[75] Inventor: John E. Franz, Crestwood, Mo.

[73] Assignee: Monsanto Company, St. Louis, Mo.

[21] Appl. No.: 926,681

[22] Filed: Jul. 21, 1978

Related U.S. Application Data

[63] Continuation-in-part of Ser. No. 753,232, Dec. 20, 1976, abandoned.

[51] Int. Cl.$^2$ ................................................ C07F 9/38
[52] U.S. Cl. ........................... 260/501.12; 260/239 B; 260/326.11 R; 260/326.85; 260/502.5; 544/110; 544/78; 546/22
[58] Field of Search .......... 260/239 B, 290 R, 293.87, 260/326.11 R, 326.85, 502.5, 501.12; 544/110, 78

[56] References Cited

U.S. PATENT DOCUMENTS

| | | | |
|---|---|---|---|
| 3,950,402 | 4/1976 | Franz | 260/502.5 |
| 3,969,398 | 7/1976 | Hershman | 260/502.5 |
| 3,977,860 | 8/1976 | Franz | 260/239 B X |

*Primary Examiner*—James O. Thomas, Jr.
*Assistant Examiner*—G. T. Breitenstein
*Attorney, Agent, or Firm*—Arnold H. Cole; Donald W. Peterson

[57] ABSTRACT

Salts of N-phosphonomethylglycine are produced by forming a salt of N-phosphonomethyliminodiacetic acid with a salt-forming cation in an aqueous medium and then oxidizing the salt solution with an oxygen-containing gas in the presence of a platinum on activated carbon catalyst. The salts produced are useful as herbicides or plant growth regulants.

17 Claims, No Drawings

PROCESS FOR PRODUCING N-PHOSPHONOMETHYLGLYCINE SALTS

This application is a continuation-in-part of copending application Ser. No. 753,232, filed Dec. 20, 1976, now abandoned.

This invention relates to a method of producing certain mono and di salts of N-phosphonomethylglycine. More particularly, the invention is concerned with a method wherein such salts are produced by an oxidation reaction which provides high yields while minimizing or eliminating disadvantages of the prior art.

The preparation of such salts by reacting N-phosphonomethylglycine with the salt-forming cations of certain metals, ammonium or organic ammonium in aqueous solution is described in U.S. Pat. No. 3,977,860. Known procedures for preparing N-phosphonomethylglycine include oxidation of N-phosphonomethyliminodiacetic acid using such oxidizing agents as hydrogen peroxide, nitric acid, peroxyacetic acid and oxidation in aqueous media, e.g., water solutions using a free oxygen-containing gas and a noble metal catalyst such as platinum, palladium, rhodium, etc. as described in U.S. Pat. No. 3,950,402 or an activated carbon catalyst as described in U.S. Pat. No. 3,969,398. According to these patents, it is preferred to employ approximately saturated solutions of the N-phosphonomethyliminodiacetic acid in water at the temperature of reaction for ease of reaction and ease of recovery of the product. The saturated aqueous solution contains at most about 1 percent by weight of the acid at 25° C., about 4 percent by weight at 95° C. and about 10 percent by weight at 150° C. Such relatively low solubility of the acid in water severely restricts the amount of N-phosphonomethyliminodiacetic acid which can be charged and oxidized in a batch reaction system to form the desired N-phosphonomethylglycine. In order to recover the N-phosphonomethylglycine from the aqueous solution, water has to be distilled off and this requires the expenditure of considerable heat energy.

It has now been found that the salts of N-phosphonomethylglycine can be readily prepared using a single aqueous reaction system in which a salt of N-phosphonomethyliminodiacetic acid is oxidized by a molecular oxygen-containing gas in the presence of a noble metal oxidation catalyst. The mono and di salts of N-phosphonomethylglycine which are produced by this method are those wherein the salt-forming cation is selected from the group consisting of the cations of alkali metals, alkaline earth metals, ammonium and organic ammonium provided that when the organic group is aryl, the ammonium salt is a primary amine salt.

The term "alkali-metal" encompasses lithium, sodium, potassium, cesium and rubidium, and the term "alkaline earth metal" includes beryllium, magnesium, calcium, strontium and barium.

The organic ammonium salts of the above type are those prepared from low molecular weight organic amines, i.e., having a molecular weight below about 300, and such organic amines include: the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-secbutylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine; primary aryl amines such as aniline, methoxyaniline, ethoxyaniline, o,m,p-toluidine, phenylenediamine, 2,4,6-tribromoaniline, benzidine, naphthylamine, o,m,p-chloroaniline, and the like; and heterocyclic amines such as pyridine, morpholine, piperidine, pyrrolidine, indoline, azepine and the like.

In the aforedescribed aqueous reaction system, the charged reactants initially form the mono or di salts of N-phosphonomethyliminodiacetic acid (depending on the stoichiometry), and these salts as formed are then oxidized to N-phosphonomethylglycine salts as indicated below for the disodium salt and the monoethylamine salt, respectively.

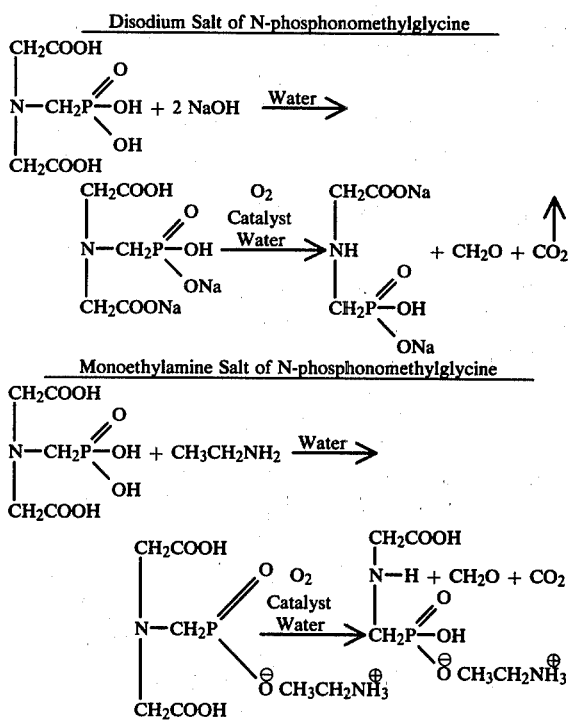

By the term "molecular oxygen-containing gas", as employed herein, is meant any gas containing molecular oxygen with or without diluents which are non-reactive with the oxygen or with the reactant or product under the conditions of reaction. Examples of such gases are air, oxygen, oxygen diluted with helium, argon, nitrogen, or other inert gas, oxygen-hydrocarbon mixtures and the like. It is preferred to employ gases containing 20 or more percent by weight molecular oxygen and even more preferred to employ gases containing 90 or more percent by weight molecular oxygen. It is, of course, obvious to those of ordinary skill in the art that when molecular oxygen-containing gases containing other inert gases are employed, the pressures should be increased to insure adequate partial pressures of oxygen in the system to maintain a sufficient rate of reaction.

The amount of the molecular oxygen-containing gas employed can vary over wide ranges. It is, of course, obvious to those skilled in the art that the best yields of the N-phosphonomethylglycine salts are produced when at least stoichiometric amounts of oxygen are employed. In most instances for ease of reaction and best yield of the final product, the amount of oxygen employed would ordinarily be at least ½ mole of oxygen for each mole of N-phosphonomethyliminodiacetic acid salt. In actual practice, the amount of oxygen employed will be from ½ to 1 or more moles for each mole of the N-phosphonomethyliminodiacetic acid salt since the efficiency of the oxygen utilization is usually less than 100 percent.

The noble metal oxidation catalyst used in the method of this invention is platinum, and such metal is supported on an activated carbon substrate. The activated carbon supports which can be employed are commercially available under a wide variety of trade names, and the manner in which the metal is placed on the substrate is well understood in the art. Many of the useful activated carbon supports are described in detail in U.S. Pat. No. 3,969,398.

In conducting the process of this invention, it is preferred to employ approximately saturated solutions of the N-phosphonomethyliminodiacetic acid salt in water at the temperature of reaction for ease of reaction and ease of recovery of the product, N-phosphonomethylglycine salt. The temperature employed in carrying out the process of this invention should be sufficient to initiate the reaction and to sustain the reaction once initiated. Temperatures of from about 25° C. to 150° C. or even higher are usually satisfactory. As those skilled in the art would realize, at lower temperatures the rate of reaction may be undesirably slow and, therefore, temperatures of at least 75° C. are preferred and even more preferred are temperatures in the range of about 90° C. to 150° C.

The oxidation reaction is conducted at superatmospheric pressures, and it is preferred that a range of about 1.5 to 5 $Kg/cm^2$ be employed. Such pressures enable the reaction to proceed to substantial completion in a relatively few hours. Use of pressures greater than 5 $Kg/cm^2$ is feasible providing the reaction vessel is properly selected.

As noted above, the related oxidation processes of the prior art employ N-phosphonomethyliminodiacetic acid as the starting material, and the very low aqueous solubility of this acid severely restricts the quantity of product which can be obtained from any given volume of water. In addition, removal of the large amounts of water by distillation in order to isolate said product requires a correspondingly large expenditure of energy.

Another problem in the prior art processes is the presence of formaldehyde which is a co-product in the oxidation reaction. This co-product must also be removed by distillation, and it is then subjected to aerobic oxidation before disposal in order to comply with environmental regulations. The presence of the formaldehyde co-product during the oxidation reaction is also undesirable since it contributes to and accelerates the formation of by-products such as N-methyl-N-phosphonomethylglycine and methylaminomethylphosphonic acid which are difficult to separate from the desired product. Although azeotropic distillation of the formaldehyde from the reaction mixture could be employed during the reaction itself, this would require added equipment and would not resolve the matter of subsequent disposal.

In accordance with the present invention, it has been found that the disadvantageous features of the prior art can be minimized or eliminated by the oxidation of a salt of N-phosphonomethyliminodiacetic acid using a platinum on activated carbon catalyst to yield a salt of N-phosphonomethylglycine.

The test procedures hereinafter described were employed to demonstrate the performance of the process of this invention. It should be understood that the specific details of each test are illustrative only and should not be construed as a limitation upon the scope of the invention. For comparison purposes, these test procedures were also carried out with various catalysts of the prior art.

For each of the runs tabulated below, the reaction vessel was a thick walled, 500 ml. glass bottle mounted on a Parr shaker. The bottle included an outer explosion shield which was wrapped with electrical heating tape, and the heating was controlled by a Variac transformer. A metal dial thermometer was inserted through a hole in the explosion shield and measured "outside" temperatures in terms of a relatively narrow range. The temperatures inside the reaction vessel itself were considered to be about 10° C. below said "outside" temperatures when the latter were measured in the 90°–110° C. range.

In each run, measured amounts of the N-phosphonomethyliminodiacetic acid and the base or cation contributor were added to 100 ml. of hot water in the bottle, the catalyst was added, and the reaction mixture was heated to a selected temperature. The bottle was pressurized with oxygen to a gauge pressure of 2.11 $Kg/cm^2$, bled down to atmospheric pressure, repressurized to the desired pressure and agitated on the shaker during the reaction period. Reaction pressure was carefully monitored, and after each increase of 0.35 $Kg/cm^2$ over the desired pressure, the reactor was bled to zero gauge pressure and then repressurized to the original starting level. This prevented an excessive accumulation of the $CO_2$ formed during the oxidation.

The course of the reaction was followed by periodic centrifugation of a small volume of the reaction mixture, acidification of the resultant clear solution with an equal volume of concentrated HCl, and determination of the proton NMR spectrum. In the tabulation of test results, the "% Unreacted Salt" in the product is based on said NMR analysis and indicates the degree of completion of the reaction in the specified time. Where "% Yield" is given, this indicates the amount of N-phosphonomethylglycine salt determined by U.V. analysis. All parts and percentages below are by weight unless otherwise stated.

| | Starting Materials (gm./100 ml H₂O) | | | Reaction Conditions | | | Reaction Product | | |
|---|---|---|---|---|---|---|---|---|---|
| Run | Acid | Base | Catalyst | hrs. | Kg/cm² | °C. | % Unreacted Salt | % Yield | Comments |
| A | 12.0 | IPA 3.15 | 5% Pt/C 0.5 | 3.0 | 2.11 | 102–109 | 9 | — | Formaldehyde = 30% theory<br>By-product I = 2–3% |
| B | 12.0 | IPA 3.15 | 5% Pt/C 1.0 | 1.5 | 2.11 | 102–110 | 0 | — | Formaldehyde = 32% theory<br>By-product I = trace<br>Very clean NMR |
| C | 18.0 | IPA 4.8 | 5% Pt/C 1.5 | 2.25 | 2.11 | 109–111 | 1 | — | Formaldehyde = 20% theory<br>By-product I = small amount<br>Clean NMR |
| D | 24.0 | IPA 6.3 | 5% Pt/C 2.0 | 2.5 | 2.11–2.81 | 108–114 | 6 | — | Formaldehyde = 14% theory<br>By-product I = 3% |
| E | 12.0 | IPA 3.15 | 5% Pt/C 1.0 | 1.75 | 2.11 | 106–110 | 0 | 98 | Formaldehyde = 30% theory<br>By-product I = trace<br>Very clean NMR |
| F | 18.0 | IPA 4.5 | 5% Pt/C 2.0 | 2.2 | 2.11 | 105–111 | 0 | 94 | Formaldehyde = 16% theory<br>By-product I = trace<br>Very clean NMR |
| G | 22.5 | IPA 5.7 | 5% Pt/C 3.0 | 2.2 | 2.11 | 105–112 | 0 | 92 | Formaldehyde = 12% theory<br>By-product I = trace<br>Very clean NMR |
| H | 27.0 | IPA 6.8 | 5% Pt/C 3.0 | 2.5 | 2.11 | 105–111 | 0 | 89 | Formaldehyde = 10% theory<br>By-product I = small amount<br>By-product II = small amount<br>Clean NMR |
| I | 4.5 | IPA 1.15 | 5% Pt/C 0.5 | 1.25 | 2.11 | 104–110 | 0 | 95 | Formaldehyde = 25% theory<br>No obvious by-products<br>Very clean NMR |
| J | 12.0 | TMA 11.5 | 5% Pt/C 1.0 | 1.25 | 2.11 | 104–112 | 0 | 95 | Formaldehyde = 1% theory<br>Very clean NMR |
| K | 13.5 | 30% NH₃ 1.0 | 5% Pt/C 1.5 | 1.5 | 2.11 | 104–106 | 0 | 92 | Formaldehyde = 20% theory<br>Very clean NMR |
| L | 12.0 | 25% DMA 9.0 | 5% Pt/C 1.0 | 1.25 | 2.11 | 104–110 | 0 | 93 | Formaldehyde = 25% theory<br>Clean NMR |
| M | 12.0 | 86% KOH 3.0 | 5% Pt/C 1.0 | 1.5 | 2.11 | 104–115 | 0 | 94 | Formaldehyde = 1% theory<br>By-product II = small amount<br>Very clean NMR |
| N | 13.5 | 86% KOH 3.7 | 5% Pt/C 1.5 | 1.0 | 2.11 | 104–112 | 0 | 96.5 | Formaldehyde = 3–4% theory<br>Very clean NMR |
| O | 4.5 | 86% KOH 1.3 | 5% Pt/C 1.0 | 17.0<br>3.0 | 2.11 | 24–26<br>26–50 | 0 | — | No formaldehyde<br>Clean NMR |
| P | 1.15 | 86% KOH 0.55 | 5% Pt/C 0.25 | 3.0 | 2.11 | 25 | 45 | — | Formaldehyde = 15–20% theory<br>Clean NMR |
| Q | 12.0 | IPA 3.15 | 5% Rh/C 0.5 | 2.0 | 2.11 | 104–109 | 11 | — | Formaldehyde = 70% theory<br>By-product I = 5–8% |
| R | 13.5 | IPA 3.35 | 5% Rh/C 1.5 | .75 | 2.11 | 104–112 | 0 | 88 | Formaldehyde = 25% theory<br>By-product I = 2–3%<br>Light yellow filtrate |
| S | 13.5 | IPA 3.35 | 5% Rh/C 1.5 | 1.0 | 2.11 | 109–110 | 0 | — | Formaldehyde = 34% theory<br>By-product I = 3–4%<br>By-product II = small amount<br>Yellow filtrate |
| T | 12.0 | IPA 3.15 | 5% Pd/C 0.5 | 3.0 | 2.11 | 102–109 | 5 | — | Formaldehyde = 36% theory<br>By-product I = 10%<br>Yellow filtrate |
| U | 13.5 | IPA 3.35 | 5% Pd/C 1.5 | 1.0 | 2.11 | 104–106 | 0 | 84 | Formaldehyde = 82% theory<br>By-product I = 2.5%<br>By-product II = trace<br>Yellow filtrate |
| V | 4.5 | IPA 1.15 | 5% Pt/Al₂O₃ 0.5<br>0.5 | 2.5<br>1.5 | 2.11<br>2.11 | 103–109<br>103–109 | 43<br>27 | —<br>— | Formaldehyde = 5% theory<br>Clean NMR |
| W | 6.0 | IPA 1.6 | F-1A 0.5 | 2.0 | 2.11 | 90–95 | 0 | 97 | Formaldehyde = 100% theory<br>By-product I = trace<br>Very clean NMR |
| X | 12.0 | IPA 3.15 | F-1A 0.6 | 2.0 | 2.11 | 102–109 | 8 | — | By-product I = 5–8% |
| Y | 12.0 | IPA 3.15 | NORIT 1.0 | 2.0 | 2.11 | 106–108 | 0 | 67 | By-product I = significant amount<br>By-product II = significant amount |
| Z | 4.5 | IPA 1.15 | NORIT 1.15 | 1.25 | 2.11 | 104–110 | 0 | 93 | Formaldehyde = 100% theory<br>By-product II = trace |
| AA | 12.0 | IPA 3.05 | F-1C 1.0 | 2.0 | 2.11 | 104–112 | 0 | 65 | By-product I = extensive<br>By-product II = extensive<br>Yellow filtrate |
| BB | 13.2 | IPA 3.35 | NORIT 1.5 | 1.07 | 2.11 | 104–109 | 2 | 78 | By-product I = significant amount<br>By-product II = significant |

| | Starting Materials (gm./100 ml H$_2$O) | | | Reaction Conditions | | | Reaction Product | | |
|---|---|---|---|---|---|---|---|---|---|
| | | | | | | | % Unreacted | % | |
| Run | Acid | Base | Catalyst | hrs. | Kg/cm$^2$ | °C. | Salt | Yield | Comments |
| CC | 13.5 | IPA 3.35 | F-6 1.5 | 3.0 | 2.11 | 104–110 | 46 | — | amount Slightly yellow filtrate Formaldehyde = 22% theory By-product I = 3.5% |
| DD | 13.5 | IPA 3.35 | F-7 1.5 | 3.0 | 2.11 | 104–110 | 29 | — | Formaldehyde = 70% theory By-product I = 9% Light yellow filtrate |
| EE | 13.5 | IPA 3.35 | F-8 1.5 | 2.0 | 2.11 | 104–112 | 20 | — | Formaldehyde = 70% theory By-product I = 6% Light yellow filtrate |
| FF | 13.5 | IPA 3.35 | F-9 1.5 | 2.0 | 2.11 | 104–112 | 15 | — | Formaldehyde = 90% theory By-product I = 5% Slight yellow filtrate |
| GG | 13.5 | IPA 3.35 | F-10 1.5 | 1.0 | 2.11 | 104–112 | 0 | 79 | Formaldehyde = 85% theory By-product I = 6% Slightly yellow filtrate Clear NMR |
| HH | 13.5 | 86% KOH 3.7 | NORIT 1.5 | 1.0 | 2.11 | 104–109 | 0 | 79 | Formaldehyde = 75% theory By-product I = 6% By-product II = trace |

In Run P, the starting materials were added to 25 ml. of hot water in a 100 ml. glass bottle. As regards the base employed, IPA designates isopropylamine, TMA designates trimethylamine and DMA designates dimethylamine. By-product I is N-methyl-N-phosphonomethylglycine, and by-product II is methylaminomethylphosphonic acid. The noble metal catalysts employed are all commercial products, and the same is true of the activated carbon catalyst Norit A. The various F designated catalysts are all activated carbons prepared as described below.

F-1A

Norit A (10 gm.), distilled water (100 ml.) and conc. HCl (100 ml.) were refluxed for 40 hours, cooled to room temperature and filtered. The residue was washed with distilled water and then with very diluted ammonia until the filtrate was neutral. The product was washed once more with a large volume of water and then dried at 100° C. for 1.5 days.

F-1C

Norit A (100 gm.), distilled water (200 ml.) and conc. HCl (100 ml.) were refluxed with stirring for 40 hours, cooled to room temperature and filtered. The product was washed and dried as described for F-1A. This product (21 gm.), distilled water (100 ml.) and conc. HCl (100 ml.) were refluxed with agitation for 40 hours, filtered hot and the residue washed with a large volume of boiling distilled water until the filtrates were neutral. The product was dried to constant weight at 115° C.

F-6

A ground mixture of sucrose (50 gm.) and urea (5 gm.) was gradually pyrolyzed in a porcelein crucible and the residue annealed at a red heat for 50 minutes. The grey-black product resembled graphite more than charcoal.

F-7

A mixture of annealed lampblack (7.5 gm.), sublimed ferric chloride (1.5 gm.), urea (5 gm.) and water (25 ml.) was concentrated at reduced pressure and the residue ground to a powder. The latter was annealed in a porcelein crucible at a red heat for 30 minutes. The cooled product was washed repeatedly with a mixture of 250 ml. of boiling water and 25–50 ml. of conc. HCl until the filtrates were colorless. The material was then washed with boiling water until the filtrates were neutral. The product was dried at 110° C. for 3 days.

F-8

A ground mixture of sucrose (50 gm.), urea (5 gm.) and sublimed ferric chloride (1.5 gm.) was gradually pyrolyzed and the residue annealed at a red heat for 30 minutes. The product was ground to a powder and extracted with hot dilute HCl until the filtrates were colorless. The residue was then washed with boiling water until the filtrates were neutral and finally dried to constant weight at 110° C.

F-9

F-8 carbon catalyst (3 gm.) was extracted with conc. HCl until the filtrates were colorless. The initial filtrates are yellow due to ferric chloride formed from iron which is not extracted with hot dilute HCl. The material was then washed with a large volume of boiling water until neutral and dried to constant weight at 110° C.

F-10

Norit A (3 gm.) was extracted with conc. HCl, washed and dried as described for F-9 catalyst.

The data presented in the table demonstrates the several advantages of the present invention. Using the low payloads which the prior art processes suggest, a comparison of Run I with Runs W and Z show the yields with the instant platinum on carbon catalyst are about the same as those with the activated carbons alone. However, said platinum on carbon catalyst provides concurrent oxidation of the formaldehyde co-product as it is formed. Thus the time and expense required to remove said co-product from the final reaction product is significantly reduced.

When the payloads are increased by a factor of two or three, Runs E, J, L and N show that the platinum on carbon catalyst continues to give a yield of desired product at a 90% or greater level. However, a similar increase in payload with an activated carbon catalyst gives yields below 80% as shown in Runs Y, AA and HH. Further, since the activated carbon catalysts alone do not provide for concurrent oxidation of the formaldehyde, the presence of the latter causes increased production of the undesirable by-products. Runs F, G and H show that still higher payloads can be employed with the platinum on carbon catalyst without any adverse effect on the % yield obtained. In addition, these higher payload runs also show relatively low levels of formaldehyde co-product with minimal by-product formation.

Returning to the increased payload Runs E, J, L and N with the platinum on carbon catalyst of this invention, it can be seen that they also compare favorably with corresponding Runs R and U which employed rhodium and palladium, respectively, on carbon. The other noble metal runs are characterized by somewhat reduced yields, along with some increase in co-product and by-product formation. The use of rhodium or palladium also gives rise to a discolored yellow filtrate in the product whereas the runs with the platinum on carbon catalyst regularly gives a colorless filtrate.

While the invention has been described herein with regard to certain representative examples for the purpose of illustrating its practice, those skilled in the art will readily recognize the variations and modifications which can be made without departing from the spirit and scope thereof.

What is claimed is:

1. Process for preparing a mono or di salt of N-phosphonomethylglycine wherein the salt-forming cation is selected from the group consisting of cations of alkali metals, alkaline earth metals, ammonium and organic ammonium, provided that when the organic group is aryl, the ammonium salt is a primary amine salt, which comprises contacting, at superatmospheric pressure, an aqueous solution of a corresponding mono or di salt of N-phosphonomethyliminodiacetic acid with an oxygen-containing gas in the presence of an oxidation catalyst which is platinum on activated carbon.

2. Process as defined in claim 1 wherein said superatmospheric pressure is at least about 1.5 Kg/cm$^2$.

3. Process as defined in claim 1 wherein said contacting is carried out at a temperature of from about 25° C. to 150° C.

4. Process as defined in claim 3 wherein said contacting is carried out at a temperature of at least about 90° C.

5. Process as defined in claim 1 wherein said salt-forming cation is alkali metal.

6. Process as defined in claim 1 wherein said salt-forming cation is said organic ammonium.

7. Process as defined in claim 1 wherein said contacting is carried out with the monoisopropylamine salt of N-phosphonomethyliminodiacetic acid.

8. Process as defined in claim 1 wherein said contacting is carried out with the mono(dimethylamine)salt of N-phosphonomethyliminodiacetic acid.

9. Process as defined in claim 1 wherein said contacting is carried out with the monopotassium salt of N-phosphonomethyliminodiacetic acid.

10. Process as defined in claim 1 wherein said contacting is carried out with the mono(trimethylamine)salt of N-phosphonomethyliminodiacetic acid.

11. Process as defined in claim 1 wherein said contacting is carried out with the monoammonium salt of N-phosphonomethyliminodiacetic acid.

12. Process as defined in claim 1 wherein said superatmospheric pressure is at least about 1.5 Kg/cm$^2$, and said contacting is carried out at a temperature of from about 90° C. to 150° C.

13. Process as defined in claim 12 wherein said contacting is carried out with the monoisopropylamine salt of N-phosphonomethyliminodiacetic acid.

14. Process as defined in claim 12 wherein said contacting is carried out with the mono(dimethylamine)salt of N-phosphonomethyliminodiacetic acid.

15. Process as defined in claim 12 wherein said contacting is carried out with the monopotassium salt of N-phosphonomethyliminodiacetic acid.

16. Process as defined in claim 12 wherein said contacting is carried out with the mono(trimethylamine)salt of N-phosphonomethyliminodiacetic acid.

17. Process as defined in claim 12 wherein said contacting is carried out with the monoammonium salt of N-phosphonomethyliminodiacetic acid.

* * * * *